(12) United States Patent
Ohta et al.

(10) Patent No.: US 7,999,234 B2
(45) Date of Patent: Aug. 16, 2011

(54) CRADLE FOR USE WITH RADIATION CONVERSION DEVICE

(75) Inventors: Yasunori Ohta, Yokohama (JP); Eiichi Kito, Minami-ashigara (JP); Naoyuki Nishino, Minami-ashigara (JP); Hiroshi Tamaoki, Odawara (JP); Tatsuo Ilyama, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 223 days.

(21) Appl. No.: 12/320,419

(22) Filed: Jan. 26, 2009

(65) Prior Publication Data
US 2009/0189098 A1 Jul. 30, 2009

(30) Foreign Application Priority Data
Jan. 29, 2008 (JP) .................. 2008-017674

(51) Int. Cl.
*G01T 1/00* (2006.01)
*H01J 43/00* (2006.01)
*H02J 7/00* (2006.01)

(52) U.S. Cl. ............. 250/363.08; 250/336.1; 250/505.1; 250/522.1; 320/107; 320/134

(58) Field of Classification Search ............. 250/363.08, 250/336.1, 505.1, 522.1; 320/107, 134
See application file for complete search history.

(56) References Cited

U.S. PATENT DOCUMENTS

| 2009/0189079 A1* | 7/2009 | Ohta et al. ................ 250/361 R |
| 2009/0189081 A1* | 7/2009 | Ohta et al. ................ 250/363.08 |
| 2009/0194695 A1* | 8/2009 | Nishino et al. ............. 250/336.1 |
| 2009/0195209 A1* | 8/2009 | Nishino et al. ................ 320/134 |

FOREIGN PATENT DOCUMENTS

| JP | 3494683 | 6/1995 |
| JP | 2000-105297 | 4/2000 |
| JP | 2000-132662 | 5/2000 |
| JP | 2006-208306 | 8/2006 |
| JP | 2008-245049 | 10/2008 |

* cited by examiner

*Primary Examiner* — Nikita Wells
(74) *Attorney, Agent, or Firm* — Jean C. Edwards, Esq.; Edwards Neils PLLC

(57) ABSTRACT

A cradle for use with a radiation conversion device includes a cradle for carrying out charging of a radiation conversion device, the cradle being disposed in the vicinity of an image capturing apparatus which captures a radiation image of a subject, the radiation conversion device detecting radiation that has passed through the subject and converting the radiation into image information. The cradle includes a charging processor for carrying out charging with respect to a battery mounted in the radiation conversion device, an image information acquisition unit for acquiring the image information from the radiation conversion device, a correction information generating unit for generating correction information with respect to the radiation conversion device using the acquired image information, and a correction information memory for storing the generated correction information in association with the radiation conversion device.

10 Claims, 4 Drawing Sheets

CRADLE FOR USE WITH RADIATION
CONVERSION DEVICE

CROSS-REFERENCE TO RELATED APPLICATIONS

The present application claims priority from Japanese Patent Application No. 2008-017674, filed Jan. 29, 2008, the contents of which are herein incorporated by reference in their entirety.

BACKGROUND OF THE INVENTION

1. Field of the Invention

The present invention relates to a cradle for use with a radiation conversion device for performing a charging process for a radiation conversion device, which is arranged in the vicinity of an image capturing apparatus for capturing a radiation image of a subject, the radiation conversion device detecting radiation that has passed through the subject and converting the radiation into image information.

2. Description of the Related Art

In the medical field, a radiation image capturing apparatus, in which radiation is applied to a subject, and radiation that has passed through the subject is directed to a radiation conversion device for capturing a radiation image of the subject, has been widely used.

In this case, a radiation conversion device (electronic cassette) has been developed in which applied radiation is converted directly into electric signals, or after the radiation has been converted into visible light by a scintillator, a solid state detecting element made up from amorphous silicon or the like is used to convert the visible light into electric signals to enable reading thereof. In such a radiation conversion device, pixels made up from a plurality of solid state detecting elements are arrayed in a matrix form, wherein by converting the radiation into image information for each pixel, a two dimensional radiation image can be obtained.

Incidentally, the conversion characteristics of each of the pixels are not all the same, and normally the conversion characteristics differ individually. Further, upon being irradiated with radiation, not only do the conversion characteristics tend to change over time, but in addition, defects may occur in which image information cannot be obtained from individual pixels.

Consequently, a technique has been proposed in which the conversion characteristics of each of the pixels are detected in order to generate correction information, such that the image information obtained when an image is captured can be corrected utilizing the correction information. (See, Japanese Laid-Open Patent Publication No. 2000-132662).

On the other hand, an internal battery may be loaded into the radiation conversion device, so as to form a portable type of device, which can be carried around. In this case, when the capacity of the internal battery is large, since the weight of the radiation conversion device also increases, inconveniences in handling of the radiation conversion device tend to occur. As a result, the storage capacity of the battery is restricted to enable a reduction in weight, whereas in the room where an image is to be captured, or in the vicinity thereof, a charging cradle is arranged, for carrying out charging of the battery at appropriate times. (See, Japanese Laid-Open Patent Publication No. 2006-208306.)

Notwithstanding, because the charging cradle disclosed in Japanese Laid-Open Patent Publication No. 2006-208306 does not have a function for generating correction information for the radiation conversion device, depending on the situation, it is thought that the charging process could be performed needlessly, with respect to a radiation conversion device that is not in a suitable condition.

SUMMARY OF THE INVENTION

A general object of the present invention is to provide a cradle for use with a radiation conversion device, in which an effective charging process can be performed with respect to a radiation conversion device.

A principal object of the present invention is to provide a cradle for use with a radiation conversion device, which can generate correction information for the radiation conversion device.

Another object of the present invention is to provide a cradle for use with a radiation conversion device, in which a correction process can be carried out with respect to image information obtained from the radiation conversion device.

A cradle for use with a radiation conversion device according to the present invention includes a cradle for carrying out charging of a radiation conversion device, the cradle being disposed in the vicinity of an image capturing apparatus which captures a radiation image of a subject, the radiation conversion device detecting radiation that has passed through the subject and converting the radiation into image information. The present invention further includes a charging processor for carrying out charging with respect to a battery mounted in the radiation conversion device, an image information acquisition unit for acquiring the image information from the radiation conversion device, a correction information generating unit for generating correction information with respect to the radiation conversion device using the acquired image information, and a correction information memory for storing the generated correction information in association with the radiation conversion device.

In accordance with the present invention, in the cradle for use with a radiation conversion device, which is disposed in the vicinity of an image capturing apparatus, an effective charging process can be performed with respect to the radiation conversion device. In addition, utilizing the image information acquired from the radiation conversion device, a process for generating correction information can be carried out. Further, with the cradle for the radiation conversion device, a correcting process can be performed with respect to the image information utilizing the generated correction information, and as a result, suitable corrected image information can be supplied.

The above and other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Figure 1:
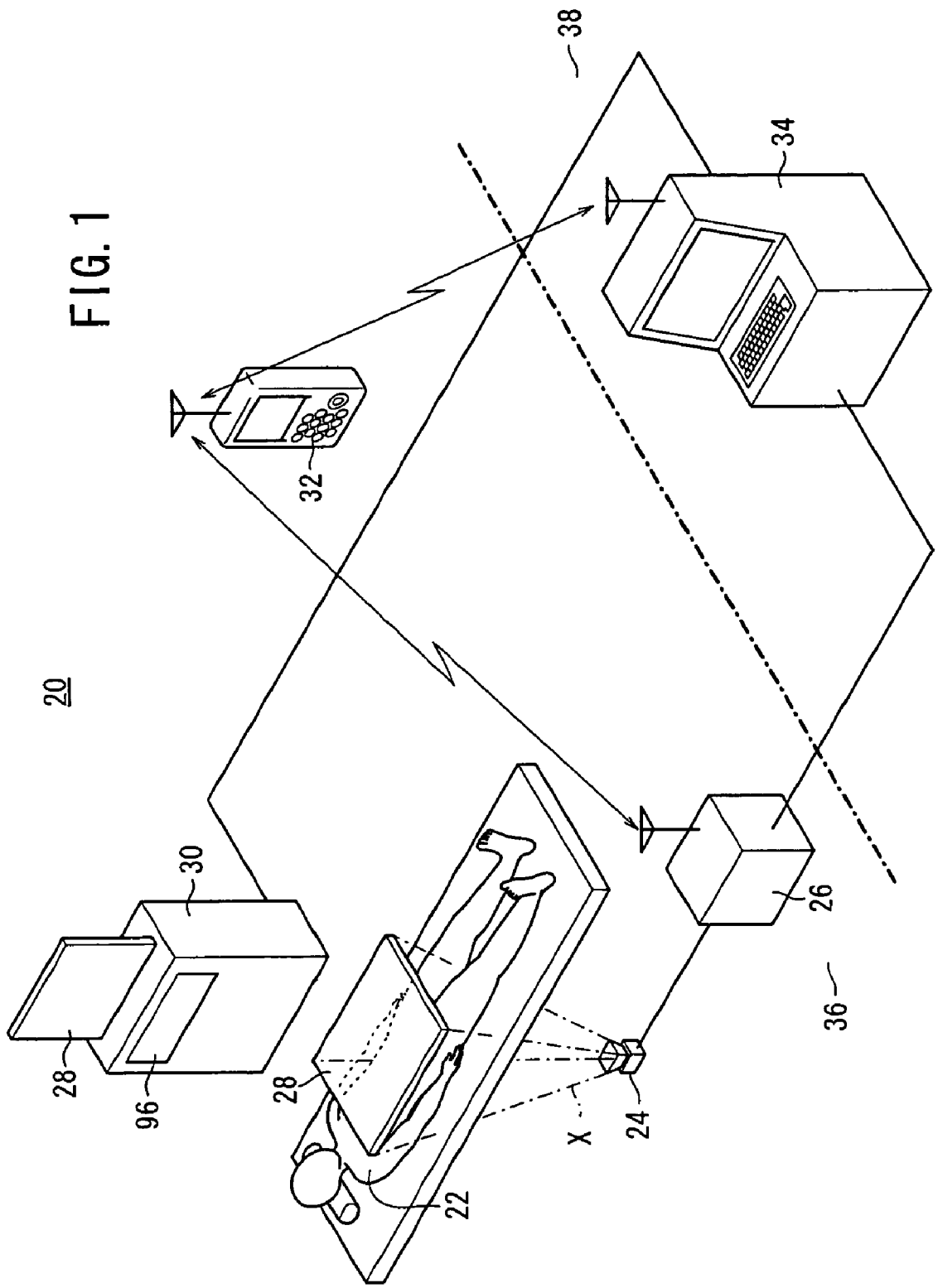
FIG. 1 is an explanatory view of a radiation image capturing system according to an embodiment of the present invention.

FIG. 1 is an explanatory view showing a radiation image capturing system 20 to which the cradle for a radiation conversion device of the present invention is applied. The radiation image capturing system 20 is equipped with a radiation source 24 for irradiating a patient 22 (subject) with radiation X having a given dose according to image capturing conditions, a radiation source control device 26 for controlling the radiation source 24, an electronic cassette 28 (radiation conversion device) for detecting radiation X that has passed through the patient 22. The radiation image capturing system 20 further comprises a cradle 30 for performing a charging process on the electronic cassette 28, for carrying out a signal transmitting and receiving process of image information based on the radiation X that is detected by the electronic cassette 28, for carrying out a correction information generating process for generating correction information for the electronic cassette 28 using the image information, and for performing a process to display the correction information, patient information (subject information), and image capturing conditions. The radiation image capturing system 20 also includes a portable information terminal 32 having an image capturing switch for the radiation source 24, and which is carried by a technician for confirming conditions including image capturing operations, and a console 34, by which the radiation source control device 26, the cradle 30, and the portable information terminal 32 are controlled, while also transmitting and receiving necessary information therebetween.

The patient information is defined as information for specifying a patient 22, such as the name and sex of the patient 22, a patient ID number, and the like. The image capturing conditions are conditions for determining a tube voltage, tube current, irradiation time, etc., for irradiating an imaging location of the patient 22 with an appropriate dose of radiation X. For example, the image capturing conditions may include the imaging location, the image capturing method, and the like. The patient information and the image capturing information can be obtained from the console 34.

The radiation source 24, the radiation source control device 26 and the cradle 30 are arranged inside of an image capturing room 36 where the image is to be captured, whereas the console 34 is disposed in an operations room 38 outside of the image capturing room 36. Further, wireless transmission of necessary information is transmitted and received between the radiation source control device 26 and the portable information terminal 32, as well as between the portable information terminal 32 and the console 34.

Figure 2:
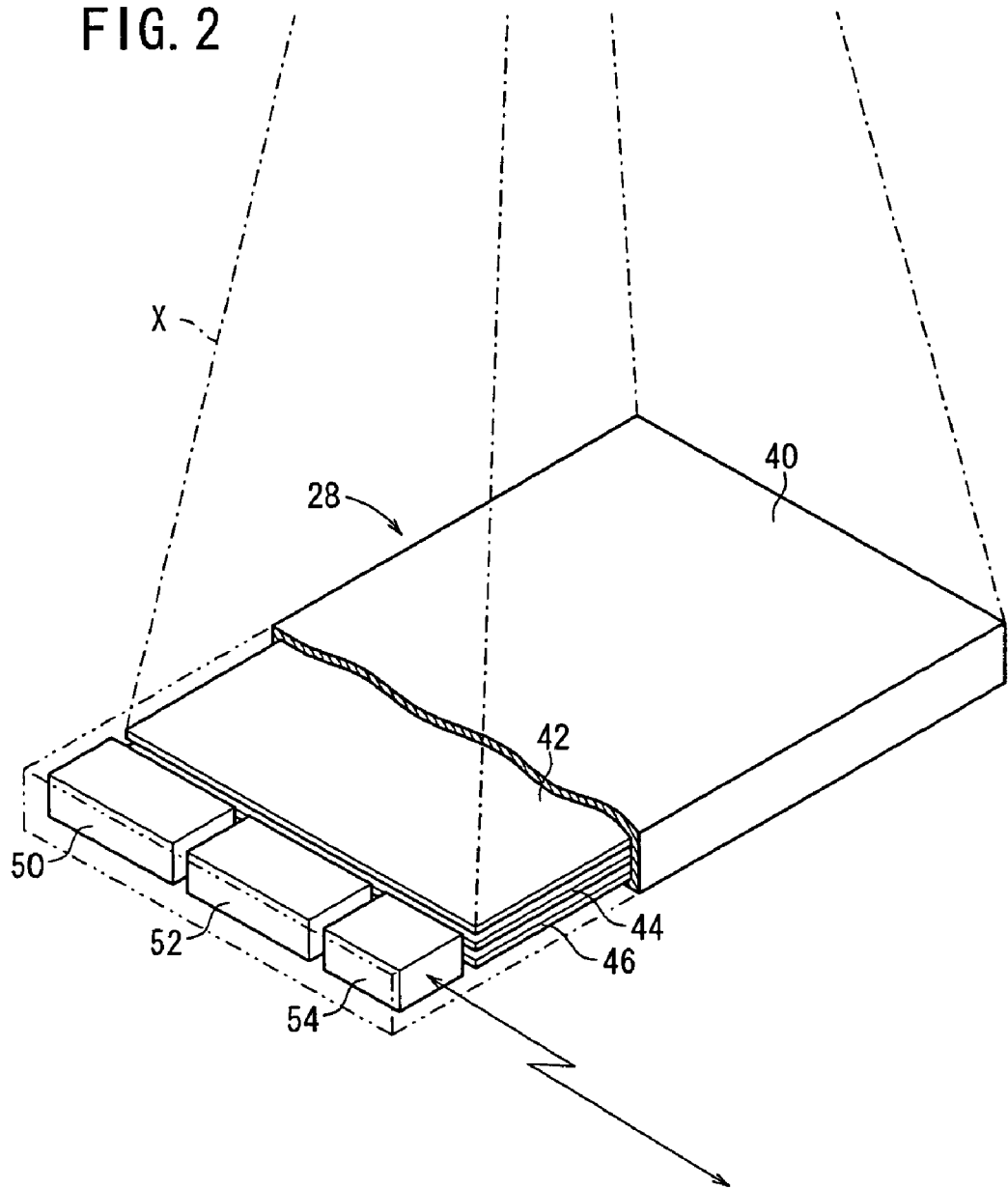
FIG. 2 is an interior structural view of an electronic cassette.

FIG. 2 is an interior structural view of the electronic cassette 28. The electronic cassette 28 is equipped with a casing 40 made from a material which is permeable to radiation X. Inside of the casing 40, a grid 42 for removing scattered radiation X from the patient 22, a radiation conversion panel 44 for detecting radiation X that has passed through the patient 22, and a lead plate 46 for absorbing backscattered radiation X are arranged in this order.

A battery 50 which serves as a power source for the electronic cassette 28, a controller 52 that controls driving of the radiation conversion panel 44 based on the power supplied from the battery 50, and a transceiver (signal transmitting/receiving unit) 54 for wirelessly transmitting signals to the cradle 30 including information converted into electrical signals from radiation X by the radiation conversion panel 44, are accommodated inside the casing 40. Moreover, in the controller 52 and the transceiver 54, for avoiding damage caused by radiation X, it is preferable for a lead plate or the like to be disposed on surface sides of the casing 40 that are subject to being irradiated with radiation X.

Figure 3:
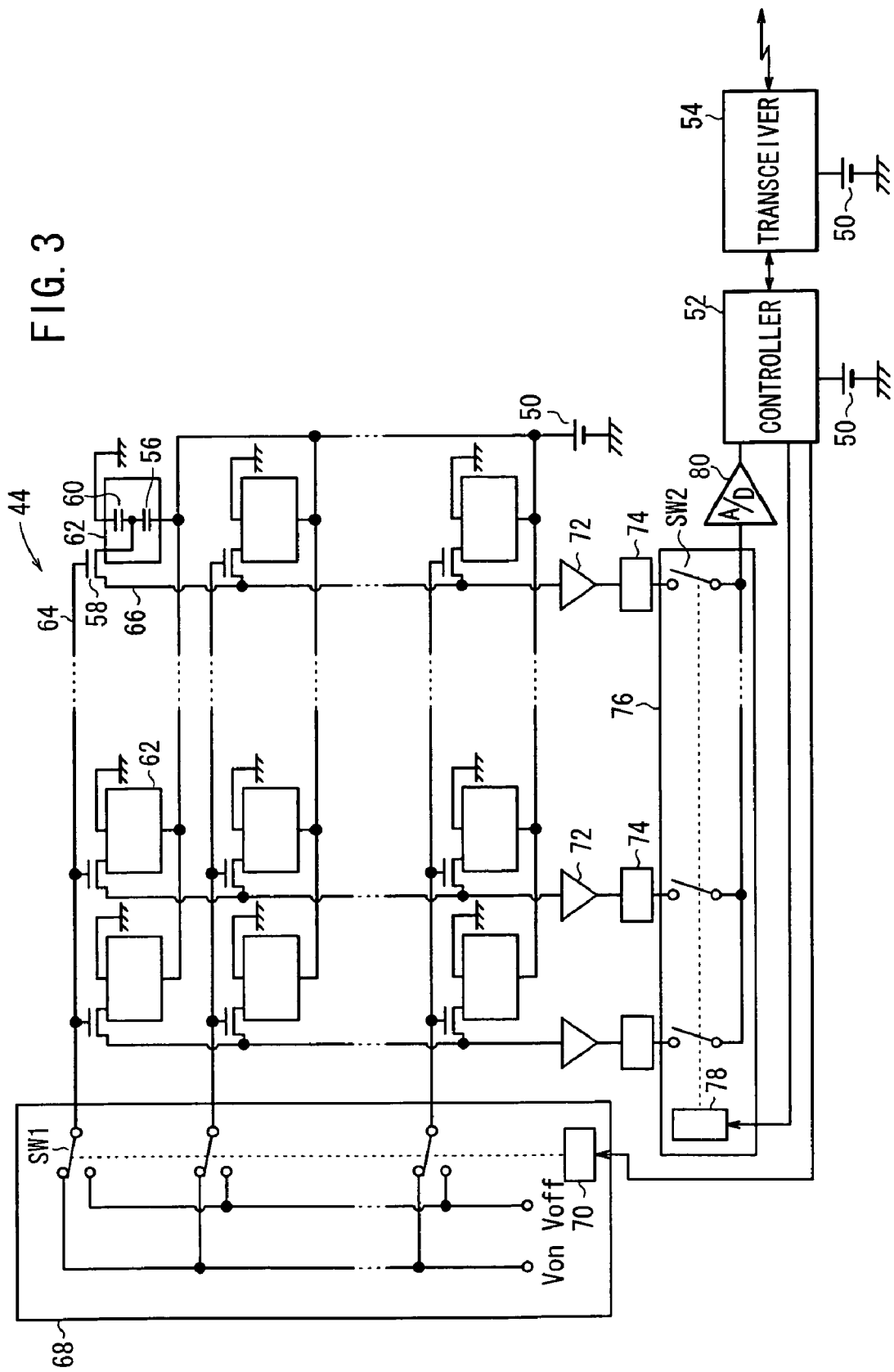
FIG. 3 is a schematic block diagram of the circuit structure of a radiation conversion panel making up the electronic cassette.

FIG. 3 is a block diagram of a circuit configuration of the electronic cassette 28 including the radiation conversion panel 44 therein. The radiation conversion panel 44 includes a structure in which a photoelectric conversion layer 56 made up from an amorphous selenium (a-Se) material or the like, which generates electric charges upon sensing radiation X, is disposed on thin film transistors (TFTs) 58 arrayed in a matrix form. After the generated electric charges are accumulated in storage capacitors 60, the TFTs 58 are successively turned on one line at a time, and the electric charges are read out as image signals. FIG. 3 shows the connected relationship of only one of the TFTs 58 and one pixel (image element) 62 made up from a photoelectric conversion layer 56 and a storage capacitor 60, whereas the structures of other similar pixels 62 have been omitted from illustration for the sake of simplicity. Since when heated to high temperatures, the structure of amorphous selenium changes and the functionality thereof is lowered, amorphous selenium must be used within a prescribed temperature range. Accordingly, it is preferable to provide some means for cooling the radiation conversion panel 44 inside the electronic cassette 28.

Gate lines 64, which extend in parallel to the direction of the rows, and signal lines 66 which extend in parallel to the direction of the columns, are connected to the TFTs 58, which are connected respectively to each of the pixels 62. Each of the gate lines 64 is connected to a line scanning driver 68, and each of the signal lines 66 is connected to a multiplexer 76 that constitutes a reading circuit.

Control signals Von, Voff that control ON and OFF states of the TFTs 58 arrayed in the direction of the rows, are supplied from the line scanning driver 68 to the gate lines 64. In this case, the line scanning driver 68 comprises a plurality of switches SW1 that switch the gate lines 64 on or off, and an address decoder 70, which outputs selection signals for selecting one of the switches SW1. Address signals are supplied from the controller 52 to the address decoder 70.

Further, the signal lines 66 are supplied with electric charges, which are stored in the storage capacitors 60 of each of the pixels 62, through the TFTs 58 arranged in the columns. The electric charges supplied to the signal lines 66 are amplified by amplifiers 72. The amplifiers 72 are connected through respective sample and hold circuits 74 to the multiplexer 76. The multiplexer 76 comprises a plurality of switches SW2 for successively switching between the signal lines 66, and an address decoder 78 for outputting a selection signal for selecting one of the switches SW2 at a time. The address decoder 78 is supplied with an address signal from the controller 52. An A/D converter 80 is connected to the multiplexer 76. A radiation image signal is converted by the A/D converter 80 into a digital image signal representing the radiation image information, which is supplied to the controller 52.

Figure 4:
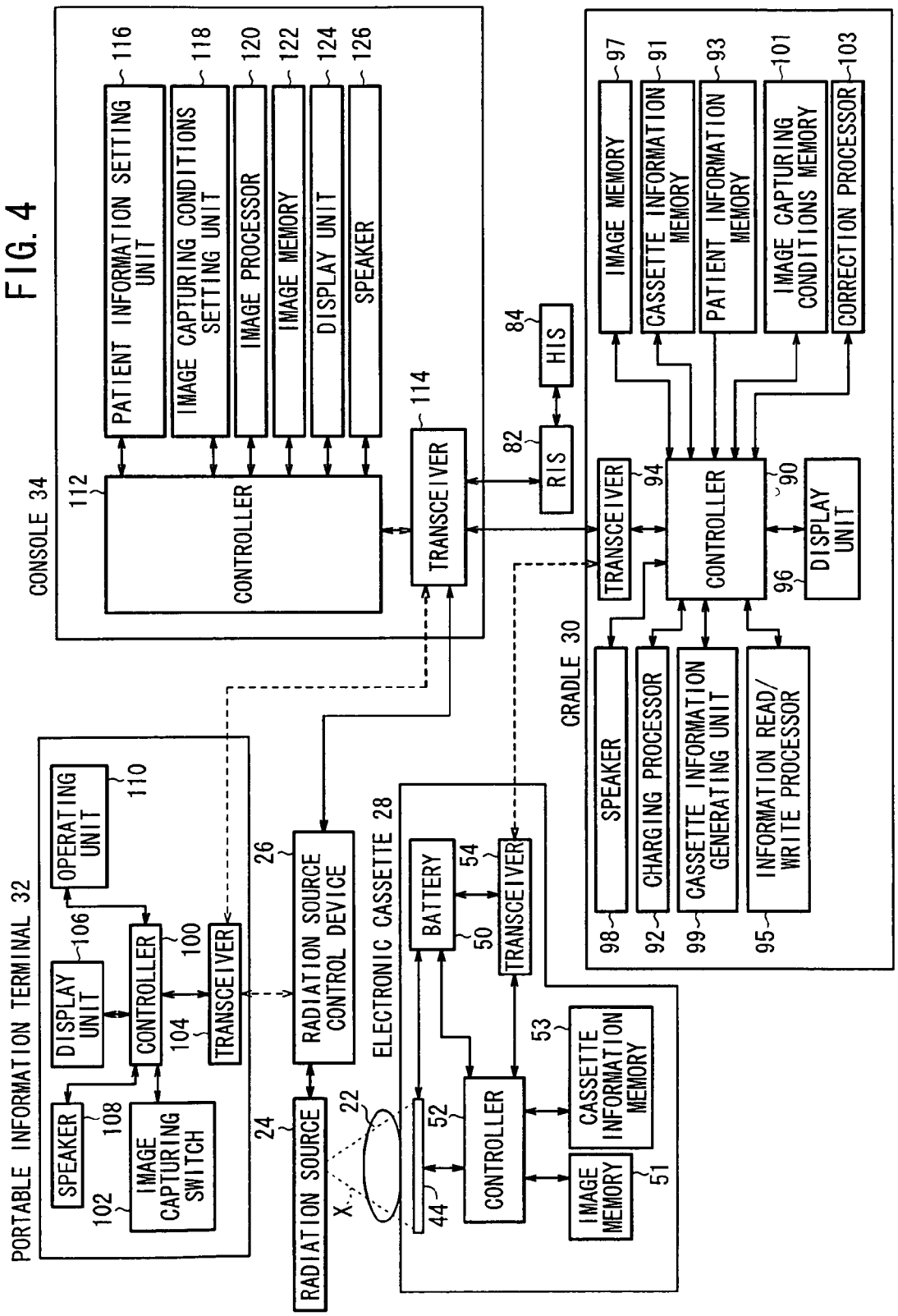
FIG. 4 is a schematic block diagram of the radiation image capturing system.

FIG. 4 is a schematic block diagram of the radiation image capturing system 20.

An image memory 51 for storing radiation image information detected by the radiation conversion panel 44, a cassette information memory 53 for storing cassette information comprising information specific to the electronic cassette 28, the transceiver (signal transmitting/receiving unit) 54, and the battery 50 that supplies power to the electronic cassette 28, are connected respectively to the controller 52 of the electronic cassette 28. The cassette information may be defined to include, for example, the number of usage times at which radiation image information has been recorded with respect to the electronic cassette 28, a cumulative exposure dose of radiation X to which the electronic cassette 28 has been exposed, and correction information, which is detected based on the radiation image information obtained from each of the pixels (image elements) 62 that make up the radiation conversion panel 44.

To a controller 90 of the cradle 30, there are connected, respectively, a charging processor 92 that carries out a charging process on the battery 50 in the electronic cassette 28 accommodated therein, a cassette information generating unit 99 that generates cassette information including correction information for the electronic cassette 28, a correction processor 103 for performing a correction process on the radiation image information utilizing the correction information, a cassette information memory 91 for storing cassette information, a patient information memory 93 and an image capturing conditions memory 101 that store patient information and image capturing conditions obtained from the console 34, an information read/write processor 95 that writes in the cassette information to the electronic cassette 28 and also reads out radiation image information from the electronic cassette 28, an image memory 97 that stores the read out radiation image information, a display unit 96 for displaying necessary information including the cassette information, patient information, image capturing conditions and acquired radiation image information, a speaker 98 for notifying a technician or the like concerning required information, and a transceiver (signal transmitting/receiving unit) 94 for carrying out transmission and reception of information between the electronic cassette 28 and the console 34. The transceiver 94 performs transmission and reception of signals by means of wireless communications. Further, the charging process carried out with respect to the battery 50 of the electronic cassette 28 can be performed in a non-contact state through the transceiver 94, or in a contact state through a non-illustrated connector provided on the electronic cassette 28 loaded into the cradle 30.

A controller 100 of the portable information terminal 32 supplies an image capturing signal generated by an image capturing switch 102 that drives the radiation source 24 to the radiation source control device 26 through a transceiver (signal transmitting/receiving unit) 104. Further, the controller 100 displays on a display unit 106 patient information, imaging capturing conditions, and the like, which are received from the console 34 through the transceiver 104, and also carries out processing for notifying a technician or the like by causing necessary information to be emitted from a speaker 108. The portable information terminal 32 includes an operating unit 110 by which necessary information can be set therein.

The console 34 is equipped with a controller 112, a transceiver (signal transmitting/receiving unit) 114 for transmitting and receiving necessary information via wireless communications with respect to the radiation source control device 26, the cradle 30 and the portable information terminal 32, a patient information setting unit 116 for setting patient information, an image capturing conditions setting unit 118 for setting required image capturing conditions for an image to be captured by the radiation source control device 26, an image processor 120 for performing image processing on the radiation image information supplied from the electronic cassette 28 via the cradle 30, an image memory 122 for storing the processed radiation image information, a display unit 124 for displaying radiation image information and other necessary information, and a speaker 126 for notifying a technician or the like concerning the necessary information.

The console 34 is connected to a radiology information system (RIS) 82, which generally manages radiation image information handled by the radiological department of a hospital along with other information. The RIS 82 is connected to a hospital information system (HIS) 84, which generally manages medical information in the hospital. Image capturing order information, including the patient information and the image capturing conditions, may be set directly by the console 34, or alternatively, can be supplied to the console 34 from an external location via the RIS 82.

The radiation image capturing system 20 according to the present embodiment is constructed basically as described above. Next, explanations shall be made concerning operations of the radiation image capturing system 20.

When a radiation image is to be captured of the patient 22, using the patient information setting unit 116 of the console 34, patient information concerning the patient 22 is set, together with setting required image capturing conditions using the image capturing conditions setting unit 118. Such information may be obtained from the RIS 82 and the HIS 84 from an upstream location via the transceiver 114. The thus set patient information and image capturing conditions can be displayed for confirmation on the display unit 124.

Next, the set patient information and image capturing conditions are transmitted from the transceiver 114 to the cradle 30, which is arranged inside the image capturing room 36, and the information is displayed on the display unit 96 of the cradle 30 by the controller 90. In this case, the technician confirms the name etc. of the patient 22, whose image is to be captured, according to the patient information displayed on the display unit 96. By means of this confirmation process, accidents such as capturing an image by mistake of the wrong patient can be prevented from occurring. Further, according to the displayed image capturing conditions, the technician can confirm the imaging region, the image capturing method, etc.

On the other hand, the electronic cassette 28 used for capturing images is loaded into the cradle 30, and a charging process on the battery 50 is carried out by the charging processor 92. The information read/write processor 95 stores patient information, pertaining to the patient 22 whose image is to be captured, in the cassette information memory 53 of the electronic cassette 28.

Further, the patient information and the image capturing conditions are transmitted from the transceiver 114 of the console 34 to the portable information terminal 32, which is carried by the technician, by means of wireless communications, and the information is displayed on the display unit 106. In this case, the technician can confirm the patient information and the image capturing conditions that are displayed on the display unit 106 of the portable information terminal 32, so that desired preparations for capturing the image can be carried out.

Furthermore, the image capturing conditions are transmitted to the radiation source control device 26. The radiation source control device 26 sets the tube voltage, the tube current, and the irradiation time, which make up image capturing conditions, in the radiation source 24, thus carrying out preparations for capturing an image.

After the technician has confirmed the patient information displayed on the display unit 96 of the cradle 30, the charging process is completed and the electronic cassette 28 in which the patient information has been stored is taken out of the cradle 30. According to the set image capturing conditions, the electronic cassette 28 is set on a desired imaging region of the patient 22.

After the electronic cassette 28 has been set in an appropriate condition with respect to the patient 22, the technician operates the image capturing switch 102 of the portable information terminal 32, whereupon capturing of the radiation image is carried out. When the image capturing switch 102 is operated, the controller 100 of the portable information terminal 32 transmits an image capturing initiation signal to the radiation source control device 26 via the transceiver 104. The radiation source control device 26 that has received the image capturing initiation signal controls the radiation source 24 according to the image capturing conditions supplied beforehand from the console 34, and thereby irradiates the patient 22 with radiation X.

The radiation X that has passed through the patient 22, after scattered rays have been removed by the grid 42 of the electronic cassette 28, irradiates the radiation conversion panel 44 and is converted into electric signals by the photoelectric conversion layer 56 of each of the pixels 62 making up the radiation conversion panel 44, which are retained as charges in the storage capacitors 60 (see FIG. 3). Next, the electric charge information that forms the radiation image information of the patient 22 stored in each of the storage capacitors 60 is read out in accordance with address signals, which are supplied from the controller 52 to the line scanning driver 68 and the multiplexer 76.

More specifically, the address decoder 70 of the line scanning driver 68 outputs a selection signal based on the address signal supplied from the controller 52, thereby selecting one of the switches SW1, and supplies a control signal Von to the gate of the TFT 58 that is connected to a corresponding gate line 64. On the other hand, the address decoder 78 of the multiplexer 76 outputs a selection signal according to the address signal supplied from the controller 52, and successively switches the switch SW2, whereby the radiation image information, which is formed as electric charge information stored in the storage capacitors 60 of each of the pixels (image elements) 62 that are connected to the gate line 64 selected by the line scanning driver 68, is read out in succession through the signal lines 66.

The radiation image information read out from the storage capacitors 60 of the pixels 62 connected to the selected gate line 64 of the radiation conversion panel 44 are amplified by respective amplifiers 72, sampled by the sample and hold circuits 74, and are supplied to the A/D converter 80 through the multiplexer 76 and converted into digital signals. The radiation image information having been converted into digital signals is temporarily stored in the image memory 51 connected to the controller 52.

Similarly, the address decoder 70 of the line scanning driver 68 successively turns on the switches SW1 according to the address signals supplied from the controller 52, and reads out the radiation image information, which is made up of charge information stored in the storage capacitors 60 of each of the pixels 62 connected respectively to the gate lines 64 through the signal lines 66, whereupon the radiation image information is stored in the image memory 51 connected to the controller 52 through the multiplexer 76 and the A/D converter 80.

Upon completion of image capturing, the electronic cassette 28 in which radiation image information of the patient 22 has been recorded is loaded into the cradle 30, which is arranged inside of the image capturing room 36. A charging process is carried out on the battery 50 by the charging processor 92, and together therewith, a process for reading out the radiation image information is performed by the information read/write processor 95. The information read/write processor 95 reads out the radiation image information stored in the image memory 51 of the electronic cassette 28, and causes such radiation image information to be stored in the image memory 97.

The cassette information generating unit 99 counts the usage times, i.e., the number of times that the cassette has been exposed to radiation X, of the electronic cassette 28 loaded into the cradle 30, and stores such information as cassette information in the cassette information memory 91. Further, based on the radiation image information stored in the image memory 97, the cassette information generating unit 99 calculates a cumulative radiation X exposure dose, from initiation of use of the electronic cassette 28 to the present time, for each of the pixels 62 of the radiation conversion panel 44, or as an averaged value of the cumulative radiation exposure dose from each of the pixels 62, and records the calculated amount in the cassette information memory 91.

Furthermore, based on the radiation image information stored in the image memory 97, the cassette information generating unit 99 calculates correction information, in accordance with the presence or absence of defective pixels, the degree of such defects or the like, for example, by comparing the radiation image information between adjacent pixels 62, and records such correction information in the cassette information memory 91. As methods for detecting defective pixels, for example, a method utilizing dark pixels (dark current), and a method utilizing radiation image information obtained by uniformly irradiating (exposing) the electronic cassette 28 to radiation X of a preset dose in a state where the patient is not disposed, may be considered. Apart from these methods, other detection methods for detecting defective pixels, which are implemented by various types of radiation image capturing apparatuses, can also be used. (Refer to Japanese Laid-Open Patent Publication No. 2008-245049.)

In the forgoing manner, the generated cassette information is displayed on the display unit 96 together with radiation image information as a preview image, which is read out from the image memory 97. Based on the displayed cassette information pertaining to the electronic cassette 28, a technician can confirm the usage state, etc., of the electronic cassette 28. In this case, for example, the charging process can be implemented only with respect to usable electronic cassettes 28. Further, based on the displayed patient information, whether or not appropriate image capturing was carried out with respect to a desired patient 22 can be confirmed inside the image capturing room 36.

The cassette information generated in the cassette information generating unit 99 of the cradle 30 is transmitted to the electronic cassette 28 and is stored in the cassette information memory 53.

Further, by displaying on the display unit 96 the number of usage times of the electronic cassette 28, the cumulative exposure dose, and defect information from the radiation conversion panel 44, etc., as read out from the cassette information memory 53, whether or not the electronic cassette 28 is in an appropriate usage condition can be confirmed.

On the other hand, the radiation image information stored in the image memory 97 of the cradle 30, after correction processing has been implemented in the correction processor 103 according to the correction information generated by the cassette information generating unit 99, is transmitted together with the patient information stored in the patient information memory 93 to the console 34 via the transceiver 94. At the console 34, after image processing has been implemented with respect to the radiation image information by the image processor 120, the radiation image information, in a state of association with the patient information, is stored in the image memory 122. Thereafter, by displaying the radiation image information stored in the image memory 122 on the display unit 124, a final confirmation of the image can be carried out.

After compression processing is implemented, as may be needed, on the radiation image information that has been transmitted to the console 34, the radiation image information may be transmitted from the transceiver 114 to the portable information terminal 32 held by the technician, so as to provide a preview image on the display unit 106. Further, a configuration can also be provided in which the radiation image information is transmitted directly to the portable information terminal 32 from the cradle 30 or the electronic cassette 28.

Of course, the present invention is not limited to the above-described embodiment, and the invention can be freely modified, within a range that does not deviate from the essence and gist of the present invention.

For example, the radiation conversion panel 44 accommodated in the electronic cassette 28 converts the radiation dose of the radiation X directly into electric signals through the photoelectric conversion layer 56. However, in place of this structure, a radiation conversion panel in which the radiation X is converted initially into visible light by a scintillator, and thereafter, the visible light is converted into electric signals using a solid-state detector element formed from amorphous silicon (a-Si) or the like, may also be used (see, Japanese Patent No. 3494683).

Further, the radiation image information can be obtained using a radiation conversion panel of a light-conversion type. With such a light-conversion type of radiation conversion panel, radiation is irradiated onto respective solid state detection elements arranged in a matrix form, and an electrostatic latent image corresponding to the irradiation dose is stored cumulatively in the solid state detection elements. When the electrostatic latent image is read, reading light is irradiated onto the radiation conversion panel, and the generated current values are acquired as radiation image information. Further, by irradiating the radiation conversion panel with erasing light, the radiation image information in the form of a residual electrostatic latent image can be erased and the radiation conversion panel can be reused (see, Japanese Laid-Open Patent Publication No. 2000-105297).

What is claimed is:

1. A cradle for use with a radiation conversion device comprising a cradle for carrying out charging of a radiation conversion device, the cradle being disposed in the vicinity of an image capturing apparatus which captures a radiation image of a subject, the radiation conversion device detecting radiation that has passed through the subject and converting the radiation into image information, the cradle further comprising:

a charging processor for carrying out charging with respect to a battery mounted in the radiation conversion device;

an image information acquisition unit for acquiring the image information from the radiation conversion device;

a correction information generating unit for generating correction information with respect to the radiation conversion device using the acquired image information; and a correction information memory for storing the generated correction information in association with the radiation conversion device.

2. The cradle for use with a radiation conversion device according to claim 1, further comprising a display unit for displaying the correction information.

3. The cradle for use with a radiation conversion device according to claim 2, wherein the display unit displays the image information obtained from the radiation conversion device.

4. The cradle for use with a radiation conversion device according to claim 1, further comprising a correction processor for performing correction processing on the image information obtained from the radiation conversion device in accordance with the correction information.

5. The cradle for use with a radiation conversion device according to claim 4, further comprising an image information transmitting unit for transmitting the image information, which has been subjected to correction processing by the correction processor, to a console.

6. The cradle for use with a radiation conversion device according to claim 1, wherein the correction information comprises defect information of respective pixels that constitute the radiation conversion device for converting the radiation into image information.

7. The cradle for use with a radiation conversion device according to claim 1, further comprising a correction information write processor by which the correction information is written to the radiation conversion device.

8. The cradle for use with a radiation conversion device according to claim 1, further comprising a usage information read processor by which usage information of the radiation conversion device is read from the radiation conversion device.

9. The cradle for use with a radiation conversion device according to claim 8, wherein the usage information comprises information concerning the number of times the radiation conversion device has been used.

10. The cradle for use with a radiation conversion device according to claim 8, wherein the usage information comprises information concerning a cumulative radiation exposure dose of the radiation with respect to the radiation conversion device.

* * * * *